(12) United States Patent
Brown

(10) Patent No.: US 7,914,570 B2
(45) Date of Patent: Mar. 29, 2011

(54) NON-SHORTENING HELICAL STENT

(75) Inventor: Brian J. Brown, Hanover, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1578 days.

(21) Appl. No.: 10/960,265

(22) Filed: Oct. 7, 2004

(65) Prior Publication Data
US 2006/0079955 A1 Apr. 13, 2006

(51) Int. Cl.
*A61F 2/06* (2006.01)
(52) U.S. Cl. ........................ 623/1.22; 623/1.15
(58) Field of Classification Search ............... 623/1.15, 623/1.22
See application file for complete search history.

(56) References Cited

U.S. PATENT DOCUMENTS

| | | | |
|---|---|---|---|
| 5,500,013 A | 3/1996 | Buscemi et al. ........... | 623/1 |
| 5,755,770 A | 5/1998 | Ravenscroft ............... | 623/1 |
| 5,824,046 A | 10/1998 | Smith et al. ............... | 623/1 |
| 5,824,053 A | 10/1998 | Khosravi et al. ........... | 623/1 |
| 5,833,699 A | 11/1998 | Chuter ..................... | 606/198 |
| 5,957,930 A | 9/1999 | Vrba ........................ | 606/108 |
| 6,019,779 A | 2/2000 | Thorud et al. ............. | 606/198 |
| 6,042,597 A | 3/2000 | Kveen et al. .............. | 606/198 |
| 6,053,940 A | 4/2000 | Wijay ....................... | 623/1 |
| 6,063,111 A | 5/2000 | Hieshima et al. .......... | 623/1 |
| 6,117,165 A | 9/2000 | Becker ..................... | 623/1 |
| 6,120,522 A | 9/2000 | Vrba et al. ................ | 606/190 |
| 6,123,712 A | 9/2000 | DiCaprio et al. ........... | 606/108 |
| 6,355,059 B1 | 3/2002 | Richter et al. ............ | 623/1.17 |
| 6,364,904 B1 | 4/2002 | Smith ....................... | 623/1.22 |
| 6,425,915 B1 | 7/2002 | Khosravi et al. ........... | 623/1.22 |
| 6,432,129 B2 | 8/2002 | DiCaprio .................. | 623/1.11 |
| 6,488,703 B1 | 12/2002 | Kveen et al. .............. | 623/1.15 |
| 6,607,552 B1 | 8/2003 | Hanson .................... | 623/1.11 |
| 6,645,237 B2 | 11/2003 | Klumb et al. .............. | 623/1.11 |
| 6,660,032 B2 | 12/2003 | Klumb et al. .............. | 623/1.13 |
| 6,736,844 B1 * | 5/2004 | Glatt et al. ................ | 623/1.22 |
| 6,746,475 B1 | 6/2004 | Rivelli, Jr. ................. | 623/1.15 |
| 2002/0082682 A1 * | 6/2002 | Barclay et al. ............ | 623/1.22 |
| 2003/0065376 A1 | 4/2003 | Seppala et al. ............ | 623/1.11 |
| 2004/0024446 A1 | 2/2004 | Smith ....................... | 623/1.15 |
| 2004/0158314 A1 | 8/2004 | Hogendijk ................ | 623/1.22 |
| 2005/0033410 A1 | 2/2005 | Hogendijk et al. ........ | 623/1.15 |

FOREIGN PATENT DOCUMENTS

| | | |
|---|---|---|
| DE | 19634241 | 2/1998 |
| EP | 0 870 483 A3 | 10/1998 |
| EP | 1 161 927 A2 | 12/2001 |
| WO | 99/48440 | 9/1999 |
| WO | 2004/058100 | 7/2004 |

* cited by examiner

*Primary Examiner* — Todd E Manahan
*Assistant Examiner* — Sarah A Simpson
(74) *Attorney, Agent, or Firm* — Vidas, Arrett & Steinkraus, P.A.

(57) ABSTRACT

A stent may comprise a helically wound ribbon of material. The stent may comprise a plurality of ribbon turns about a longitudinal axis of the stent. Upon expansion of the stent, the diameter of the stent may increase and the number of ribbon turns may decrease. Upon expansion of the stent, the width of the ribbon may increase. The length of the stent may be the same in unexpanded and expanded states.

9 Claims, 6 Drawing Sheets

NON-SHORTENING HELICAL STENT

BACKGROUND OF THE INVENTION

The use of stents in bodily lumen is well known. A stent is typically delivered in an unexpanded state to a desired location in a bodily lumen via a medical device such as a catheter. Once the stent is at the desired bodily location, it is either expanded with a balloon or other suitable device or allowed to expand by, for example, withdrawing a restraining sheath.

Helical or spiral wound stents are generally known, such as disclosed in U.S. Pat. No. 6,042,597, the entire disclosure of which is incorporated herein by reference. Helical stents may exhibit undesirable effects due to shape changes upon expansion. For example, as a helical stent unwinds during expansion, it may experience a large amount of foreshortening or reduction in length. Helical stents may also have relatively large gaps between windings in an expanded state. In some cases, large gaps may result in poor vessel wall support and even tissue prolapse.

There remains a need for helical or wound stents having desirable flexibility which experience minimal foreshortening upon expansion and provide suitable vessel support in an expanded state.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In one embodiment, a helical stent may comprise a helically wound ribbon of material. The stent may have a longitudinal axis extending therethrough. The ribbon may have a longitudinal width as measured in a direction parallel to the longitudinal axis of the stent. The longitudinal width of the ribbon in an expanded state of the stent may be greater than the longitudinal width of the ribbon in an unexpanded state of the stent.

In another embodiment, a stent may comprise a helically wound ribbon. The ribbon may comprise a plurality of turns about a central longitudinal axis of the stent. Each turn of the ribbon may have a width. The width of each turn may increase upon expansion of the stent.

In another embodiment, a stent may comprise a strip helically wound about a longitudinal axis of the stent. The strip may have a longitudinal width as measured in a direction parallel to the longitudinal axis of the stent and a predetermined number of turns about the longitudinal axis. Upon expansion of the stent, the number of turns of the strip about the longitudinal axis may decrease and the longitudinal width of the strip may increase.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there are illustrated and described various embodiments of the invention.

BRIEF DESCRIPTION OF THE DRAWINGS

A detailed description of the invention is hereafter described with specific reference being made to the drawings.

DETAILED DESCRIPTION OF THE INVENTION

Figure 1:
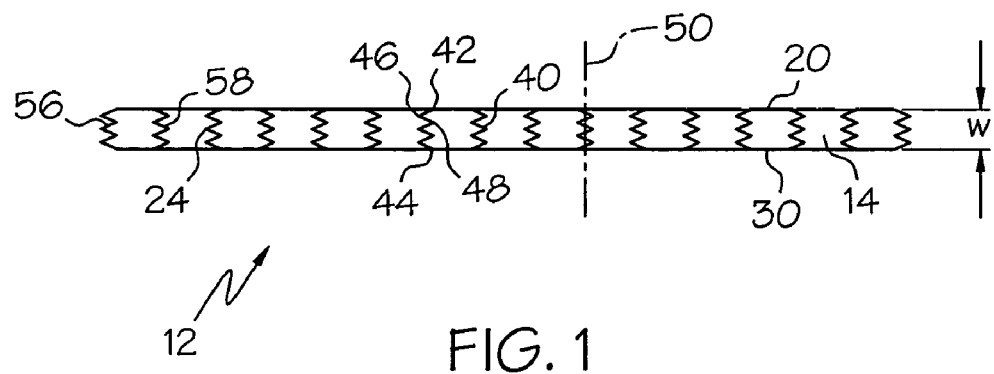
FIG. 1 shows an embodiment of a strip or ribbon in an unexpanded state.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

For the purposes of this disclosure, the terms "spiral" and "helical" are intended to encompass shapes that wind about a longitudinal axis for at least one turn, and desirably a plurality of turns. Spiral or helical shapes may include, but are not limited to, pure spiral shapes, pure helical shapes, and shapes which may have a substantially spiral or helical shape but may also include local derivations from a purely spiral or helical shape. Further, in some embodiments, a spiral or helix may include a non constant pitch with respect to the longitudinal axis. A pure helix may be a space curve with parametric equations $x = r \sin t$; $y = ct$; and $z = k = r/(r^2 + c^2)$; where r is the radius of the helix and c is a constant giving the separation of the loops of the helix.

Figure 2:
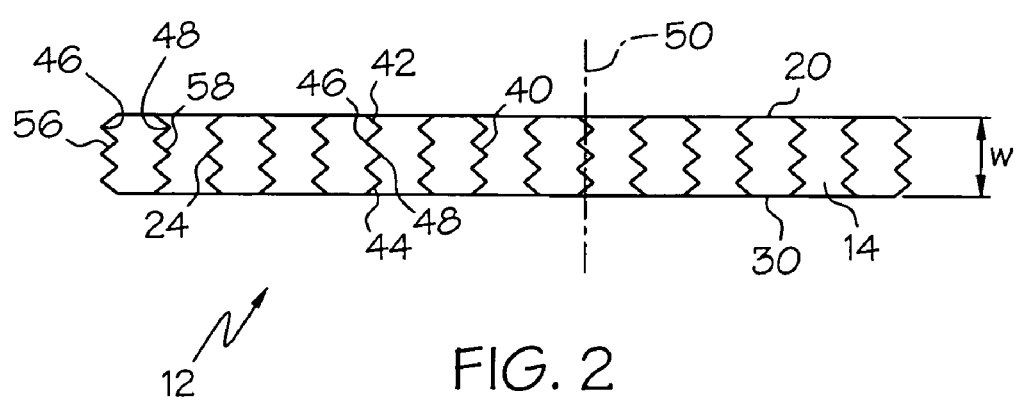
FIG. 2 shows an embodiment of a strip of ribbon in an expanded state.

FIGS. 1 and 2 show one embodiment of an unwound strip or ribbon 12 which may be wound to form a helical stent. The ribbon 12 may comprise a framework having a plurality of cells 14. The ribbon 12 may include a first rail or edge member 20 and a second rail or edge member 30. In some embodiments, the first rail 20 may be parallel to the second rail 30.

Any portion of the ribbon 12 may have a width dimension 'w' or spacing between the first rail 20 and the second rail 30. When the first rail 20 and second rail 30 are parallel, the ribbon 12 may have a constant width w. At least one and desirably a plurality of connector struts 40 may connect the first rail 20 to the second rail 30.

Figure 7:
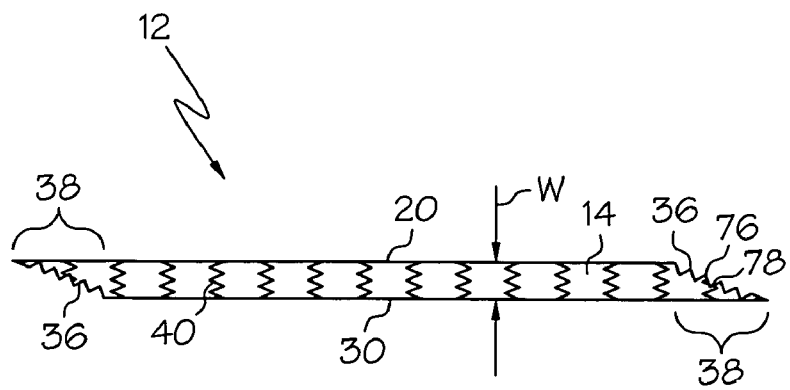
FIG. 7 shows another embodiment of a strip or ribbon.

It is also within the scope of the invention for the rails to be non-parallel to one another. In such an embodiment, the width of the ribbon would not be constant. The rails may uniformly spiral or may have a substantially spiral shape with local deviations from a pure spiral shape. As an example of the latter, one or more rails may have a plurality of peaks and valleys, but may have a shape which is substantially spiral. For example, FIG. 7 shows an embodiment of a ribbon 12 wherein the rails 20, 30 have peaks 66 and valleys 68. The ribbon 12 may be wound helically to form a stent.

Connector struts 40 may be coupled at a first end 42 to the first rail 20 and may be coupled at a second end 44 to the second rail 30. Connector struts 40 may include at least one peak 46 and/or at least one valley 48. In some embodiments, a connector strut 40 may include a plurality of peaks 46 and a plurality of valleys 48. The first end 42 or the second end 44 of a connector strut 40 may extend from a respective rail 20, 30 in a direction perpendicular to the rail 20, 30 or at any non-zero angle to the rail 20, 30.

Each connector strut 40 may include a connector strut axis 50. A connector strut 40 may span between the first rail 20 and the second rail 30 across the width of the ribbon 12 or in a direction such that the connector strut axis 50 is generally perpendicular to the rails 20, 30. In some embodiments, a connector strut 40 may span between the first rail 20 and the second rail 30 such that the connector strut axis 50 is oriented at an angle to at least one rail 20 and/or rail 30.

Adjacent connector struts 40 may be similar to one another or may have varying geometries. In some embodiments, all of the connector strut axes 50 may be parallel to one another. In some embodiments, various connector strut axes 50 may be nonparallel to one another. In some embodiments, one or more connector struts 40 may be mirror images of other connector struts or may have a reversed orientation when compared to other connector struts. For example, as shown in FIG. 2, a first connector strut 56 may be oriented in one direction and may have a peak 46 in proximity to the first rail 20, while a second connector strut 58 may be oriented in another direction and may have a valley 48 in proximity to the first rail 20.

FIG. 1 shows an embodiment of an unwound ribbon 12 in a first or unexpanded state. FIG. 2 shows an embodiment of an unwound ribbon 12 in a second or expanded state. The length of a ribbon 12 may remain substantially the same before and after expansion. Desirably, the width w of a ribbon 12 in an expanded state is greater than the width w of the ribbon 12 in an unexpanded state. Upon expansion of a ribbon 12, the shape of a connector strut 40 may change and the length of a connector strut 40 along its connector strut axis 50 may increase.

Figure 3:
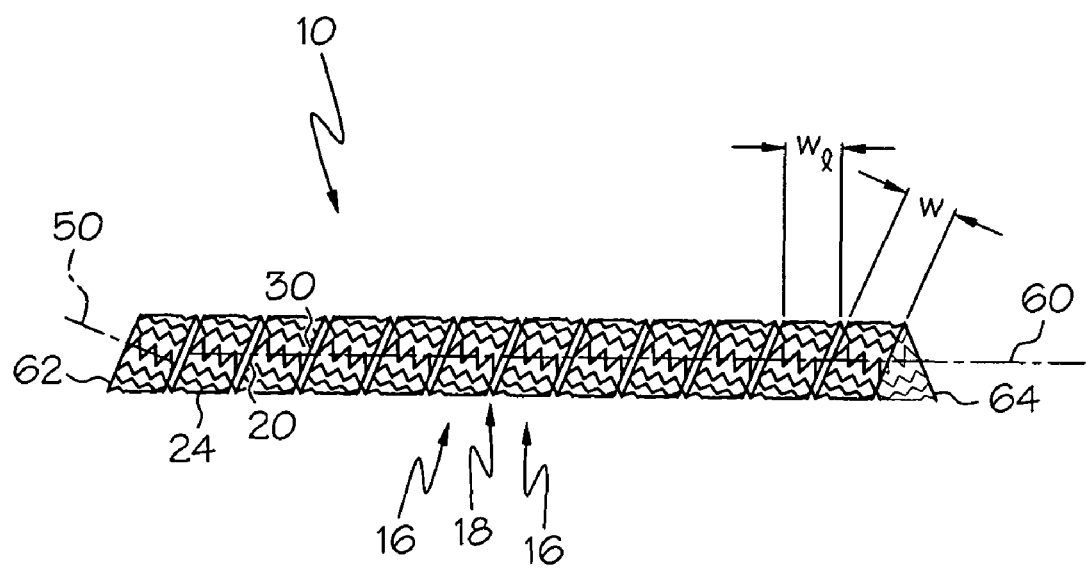
FIG. 3 shows an embodiment of a stent comprising a helically wound ribbon in an unexpanded state.
Figure 4:
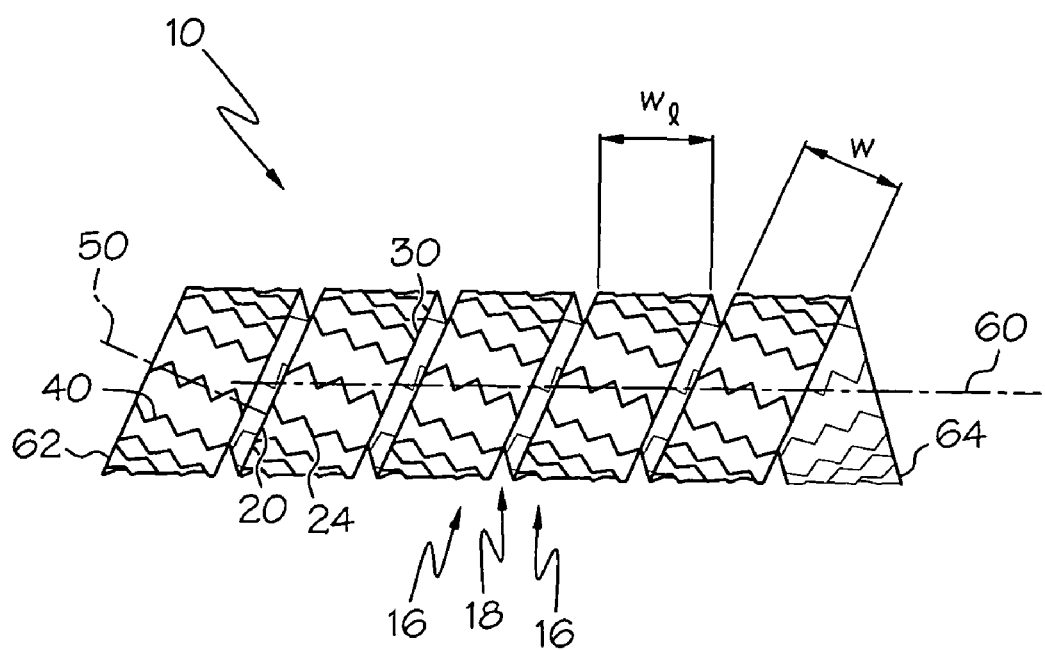
FIG. 4 shows an embodiment of a stent comprising a helically wound ribbon in an expanded state.

FIGS. 3 and 4 show embodiments of a ribbon 12 wound helically to form a stent 10. The ribbon 12 may include any of the features disclosed herein. The stent 10 may have a longitudinal axis 60 and may comprise an expandable framework. The stent 10 may have a number of ribbon turns 16. Each ribbon turn 16 may comprise a portion of the ribbon 12.

The stent 10 may include a gap 18 which may spiral continuously from a first end 62 of the stent 10 to a second end 64. A gap 18 may comprise space between adjacent ribbon turns 16. In some embodiments, a gap 18 may comprise space between a first rail 20 and a second rail 30 that is external to the ribbon 12, wherein no connector struts 40 are located.

A gap 18 may spiral for any amount of rotational measurement. For example, a gap 18 may spiral continuously for 360°, 540°, 720°, 1080°, 4320° or more. The gap 18 may spiral over less than a complete turn, over a complete turn or over integral or non-integral multiples of complete turns.

A ribbon 12 or ribbon turn 16 may further have a longitudinal width '$w_l$', as measured in the longitudinal direction of the stent 10. The longitudinal width $w_l$ is the distance between a first rail 20 and a second rail 30, as measured in a direction parallel to the stent longitudinal axis 60. Generally, the longitudinal width $w_l$ of a ribbon 12 will be larger than the width w of the ribbon.

Connector struts 40 may be oriented such that a connector strut axis 50 is at a non-zero angle with respect to the longitudinal axis of the stent 10. In some embodiments, at least one connector strut 50 may be oriented such that the connector strut axis 50 is parallel to the longitudinal axis of the stent 10.

FIG. 3 shows an embodiment of a ribbon 12 wound helically to form a stent 10 in a first or unexpanded state. The stent 10 may have a predetermined number of turns 16, a length and a diameter.

FIG. 4 shows an embodiment of a ribbon 12 wound helically to form a stent 10 in a second or expanded state. Upon expansion, the diameter of the stent 10 may increase and the number of turns 16 along the length of the stent may decrease. For example, an unexpanded stent 10 may have twice as many turns as the stent 10 after expansion.

Upon expansion of the stent 10, the ribbon 12 may also expand, wherein the shape of a connector strut 40 may change and the length of a connector strut 40 along its connector strut axis 50 may increase. Thus, the longitudinal width $w_l$ of the ribbon 12 or a ribbon turn 18 may increase upon expansion.

Desirably, the overall length of the stent 10 will be substantially similar in an unexpanded state and in an expanded state.

A ribbon 12 may comprise a plurality of loops 24. Each loop 24 may have a longitudinal length component, or span in a direction parallel to the longitudinal axis of the stent 10. Upon expansion of the stent 10, the longitudinal length component of a loop 24 may increase, or a loop 24 may lengthen a direction parallel to the longitudinal axis of the stent 10.

Figure 5:
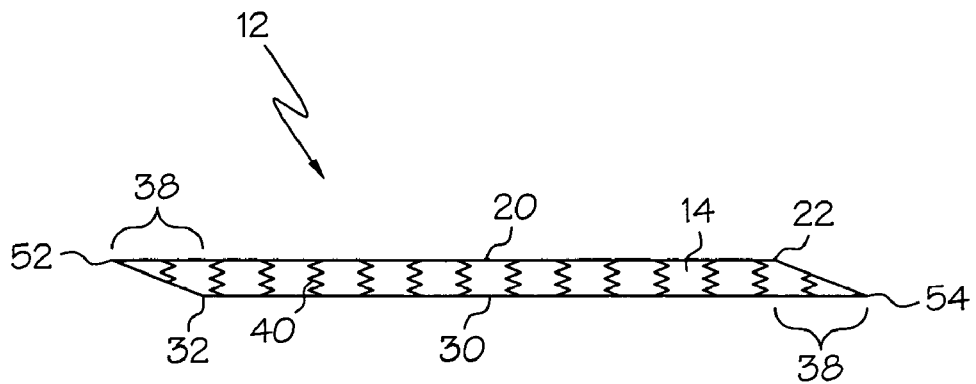
FIG. 5 shows another embodiment of a ribbon.

FIG. 5 shows another embodiment of an unwound strip or ribbon 12 which may be wound to form a helical stent. The width w of the ribbon 12 may vary along the length of the ribbon 12. The ribbon 12 may comprise a framework having a plurality of cells 14. The ribbon 12 may include a first rail or edge member 20 and a second rail or edge member 30. A portion of the first rail 20 may be parallel to a portion of the second rail 30. Any portion of the ribbon 12 may have a width dimension 'w' or spacing between the first rail 20 and the second rail 30. The first rail 20 may include at least one bend 22 and the second rail 30 may include at least one bend 32. The first rail 20 may contact the second rail 30 at a first end 52 and at a second end 54 of the ribbon 12.

Each end of the ribbon 12 may include a tapered portion 38, wherein the first rail 20 and the second rail 30 may be non-parallel. Each end of the ribbon 12 may taper to a point. Tapered end portions 38 may allow a ribbon 12 to be helically wound to form a stent 10 wherein the ends of the stent may be orthogonal to the longitudinal axis of the stent 10.

Figure 6:
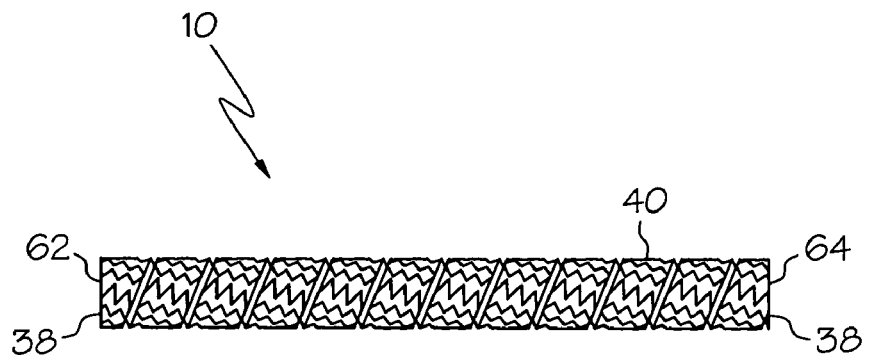
FIG. 6 shows another embodiment of a stent comprising a helically wound ribbon.

FIG. 6 shows an embodiment of a ribbon 12 having tapered end portions 38 wound helically to form a stent 10. The stent 10 may have a generally cylindrical shape. A first end of the stent 62 and a second end of the stent 64 may be orthogonal to the longitudinal axis of the stent 10.

FIG. 7 shows another embodiment of an unwound strip or ribbon 12 which may be wound to form a helical stent. The width w of the ribbon 12 may vary along the length of the ribbon 12. The ribbon 12 may comprise a framework having a plurality of cells 14. The ribbon 12 may include a first rail or edge member 20 and a second rail or edge member 30. At least a portion of the first rail 20 may be parallel to a portion of the second rail 30.

The ribbon 12 may include at least one end connector 36. An end connector 36 may connect to an end of a rail 20, 30. In some embodiments, an end connector 36 may connect at one end to an end of the first rail 20 and at the other end to an end of the second rail 30.

An end connector 36 may extend at any angle with respect to a rail 20, 30. In some embodiments, an end connector 36 may include peaks 76 and/or valleys 78. In some embodiments, a connector strut 40 may connect to an end connector 36. A connector strut 40 may connect to any portion of an end connector 36, including peaks 76 and valleys 78.

Each end of the ribbon 12 may include a tapered portion 38. Each end of the ribbon 12 may taper to a point. Tapered end portions 38 may allow a ribbon 12 to be helically wound to form a stent 10 wherein the ends of the stent may be orthogonal to the longitudinal axis of the stent 10.

Figure 8:
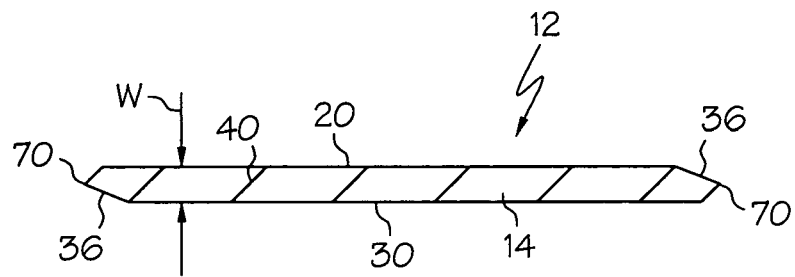
FIG. 8 shows another embodiment of a strip or ribbon in an unexpanded configuration.

FIG. 8 shows another embodiment of a ribbon 12 which may be wound to form a stent 10. The ribbon 12 is shown in an unexpanded state. The ribbon 12 may comprise a framework having a plurality of cells 14. The ribbon 12 may include a first rail or edge member 20 and a second rail or edge member 30. In some embodiments, the first rail 20 may be parallel to the second rail 30. Any portion of the ribbon 12 may have a width dimension 'w'.

At least one and desirably a plurality of connector struts 40 may connect the first rail 20 to the second rail 30. A connector strut 40 desirably extends at a non-zero angle with respect to a rail 20, 30.

The ribbon 12 may further include end connectors 36, which may connect at one end to an end of the first rail 20 and at the other end to an end of the second rail 30. An end connector 36 may include a bend 70, or in some embodiments may include curvature and/or an arcuate shape.

Figure 9:
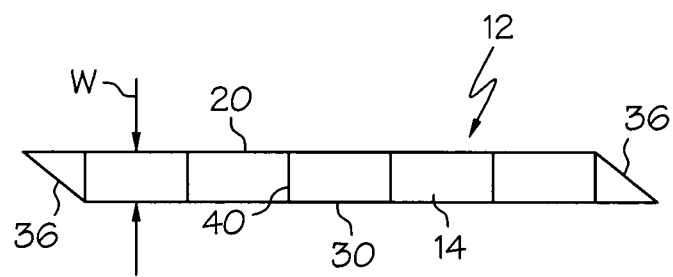
FIG. 9 shows the ribbon of FIG. 8 in an expanded configuration.

FIG. 9 shows the ribbon of FIG. 8 in an expanded configuration. The width w in an expanded configuration is desirably greater than the width w in an unexpanded configuration. The connector struts 40 desirably extend from a rail 20, 30 at a greater angle in the expanded state than in an unexpanded state, up to a maximum of 90°. For example, in an expanded state, connector struts 40 may extend orthogonally with respect to a rail 20, 30, while in an unexpanded state, the connector struts 40 may extend at an angle of less than 90°.

In some embodiments, end connectors 36 may straighten as the ribbon 12 expands. In some embodiments, the end connectors 36 may extend from a rail 20, 30 at an angle of less than 90° when the ribbon 12 is expanded.

Figure 10:
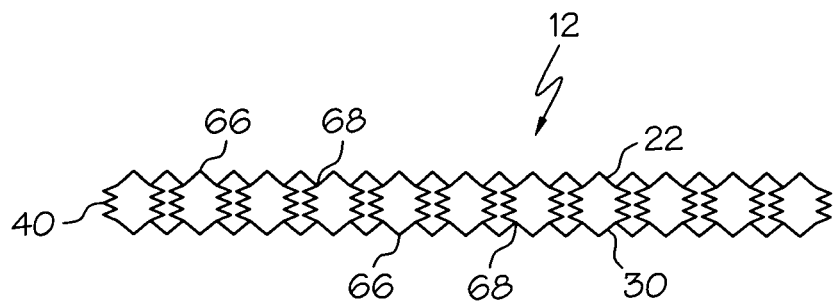
FIG. 10 shows another embodiment of a strip or ribbon.

FIG. 10 shows another embodiment of a ribbon 12 which may be wound helically to form a stent 10. The ribbon 12 may have a first rail 20 and a second rail 30. Each rail 20, 30 may have at least one and desirably a plurality of peaks 66 and valleys 68. Connector struts 40 may connect to any portion of a rail 20, 30, including at either end, at a peak 66, at a valley 68, or any intermediate location between a peaks and a valley.

When a stent 10 includes rails 20, 30 having a plurality of peaks 66 and valleys 68, the rails 20, 30 may maintain the peaks 66 and valleys 68 during and after expansion of the stent 10. However, in some embodiments, upon expansion of the stent 10, the peaks 66 and valleys 68 may straighten, leaving rails 20, 30 which may comprise a pure spiral shape, for example as shown in FIG. 4.

When the ribbon 12 of FIG. 10 expands, both the length and the width of the ribbon 12 may increase. Peaks 66 and valleys 68 in each rail 20, 30 allow the ribbon 12 to lengthen during expansion. The overall length of a stent 10 formed by a helically wound ribbon 12 may be substantially the same in the unexpanded and expanded configurations.

Figure 11:
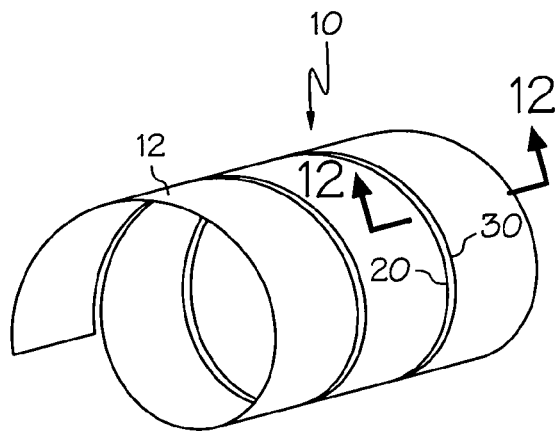
FIG. 11 shows a generic schematic of a stent formed by a helically wound ribbon.
Figure 12:
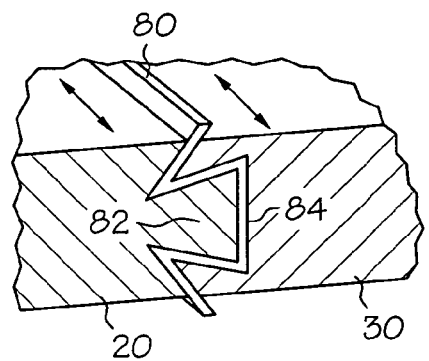
FIG. 12 shows a sectional view of an embodiment of a first rail and a second rail. The view may be taken along line A-A of FIG. 11.
Figure 13:
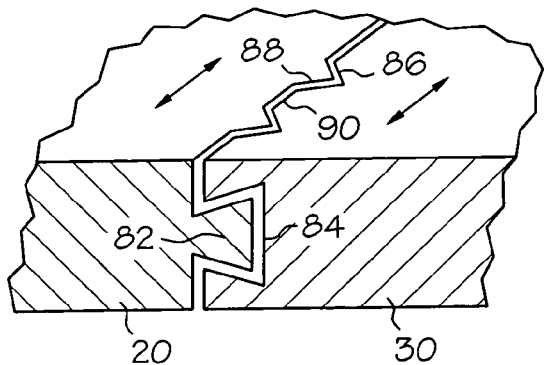
FIG. 13 shows another sectional view of an embodiment of a first rail and a second rail. The view may be taken along line A-A of FIG. 11.
Figure 14:
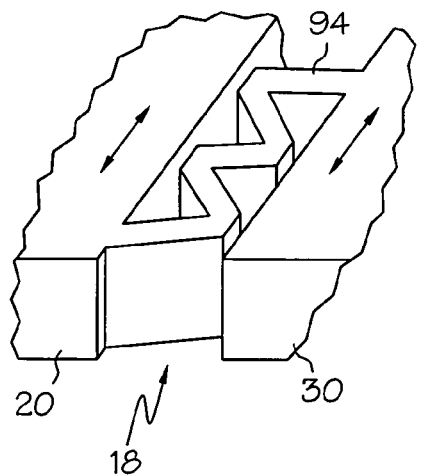
FIG. 14 shows another sectional view of an embodiment of a first rail and a second rail. The view may be taken along line A-A of FIG. 11.

FIG. 11 shows a schematic of a ribbon 12 wound to form a stent 10. In some embodiments, a first rail 20 and a second rail 30 may be slidably engaged with one another when the ribbon 12 is wound helically. FIGS. 12-14 show various embodiments of mechanisms for engagement between the first rail 20 and the second rail 30. The views of FIGS. 12-14 may be taken from various embodiments of a stent 10 along line A-A as shown in FIG. 11.

FIG. 12 shows a sectional detail of an embodiment of a first rail 20 and a second rail 30 which may be slidably engaged. The first rail 20 may include a first mating portion 82 and the second rail 30 may include a second mating portion 84. The first mating portion 82 may engage the second mating portion 84. Desirably, when the first mating portion 82 is engaged with the second mating portion 84, the first rail 20 may slide along its longitudinal axis with respect to the second rail 30, but will not translocate in directions orthogonal to its longitudinal axis with respect to the second rail 30. Thus, the first rail 20 may move in a spiral direction with respect to the second rail 30. In some embodiments, the second mating portion 84 may comprise a shaped groove, and the first mating portion 82 may comprise a flange that may be shaped similarly to the shaped groove.

In some embodiments, an insulating member 80 may be inserted between adjacent turns of the stent 10, for example between the first rail 20 and the second rail 30. An insulating member 80 may be used to reduce the possibility of an MRI artifact being developed when viewing the stent 10 under MRI. An insulating member 80 may be made from any suitable material, such as nonconductive material. Some examples include ceramics, non-conductive polymers, poor conductors, latex, rubber, silicon rubber, Pebax®, urethane, pelothane, Tecothane®, polyester isobutyl styrene, epoxies and thermoplastics. When the first rail 20 is shaped to engage the second rail 30, at least a portion of the insulating member 80 may be placed between the first mating portion 82 and the second mating portion 84.

FIG. 13 shows a sectional detail of another embodiment of a first rail 20 and a second rail 30 which may be slidably engaged. The first rail 20 may include a first mating portion 82, and the second rail 30 may include a second mating portion 84. The rails 20, 30 may further include an incremental adjustment mechanism which may prevent sliding of the rails with respect to one another unless a predetermined amount of force is applied to the rails 20, 30. In one embodiment, an incremental adjustment mechanism may comprise a series of grooves 86 in the second rail 30 and at least one detent 88 in the first rail 20. The detent 88 may incrementally move between adjacent grooves 86 as the stent 10 expands. In another embodiment, each rail 20, 30 may include a plurality of shaped teeth 90, which may be oriented in opposite directions, which are arranged to allow incremental movement of the first rail 20 with respect to the second rail 30. An incremental adjustment mechanism may be desirable for embodiments of a stent 10 that are balloon expandable or at least partially balloon expandable.

FIG. 14 shows another embodiment of a first rail 20 engaged with a second rail 30. A gap connector 94 may connect at one portion to the first rail 20 and at another portion to the second rail 30. A gap connector 94 may be located in a gap 18 between the first rail 20 and the second rail 30. Desirably, a gap connector 94 is arranged to lengthen as the first rail 20 translocates with respect to the second rail 30. Therefore, a gap connector 94 may include a plurality of peaks and valleys. A gap connector 94 may limit movement of the first rail 20 with respect to the second rail 30 in stent longitudinal and/or radial directions.

Figure 15:
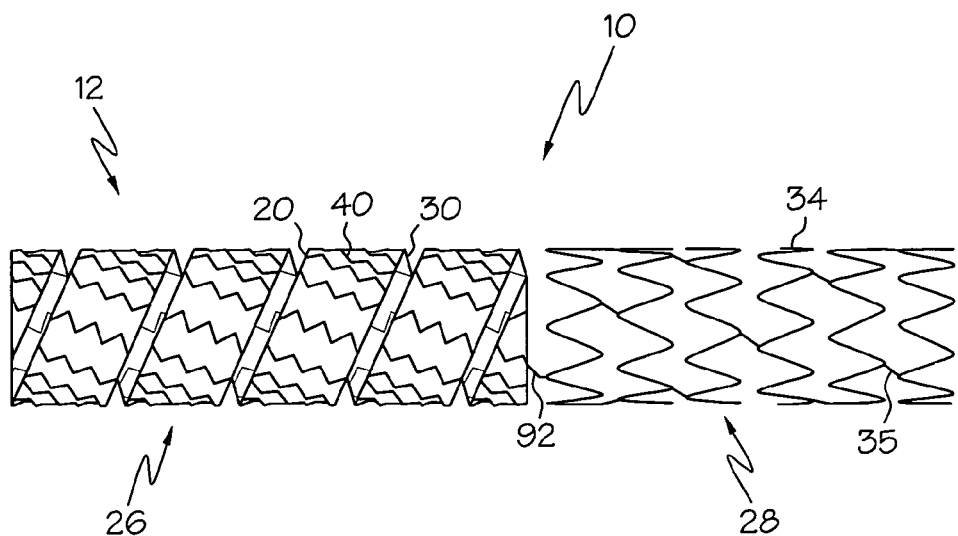
FIG. 15 shows another embodiment of an inventive stent.

FIG. 15 shows another embodiment of a stent 10, wherein a first portion 26 of the stent 10 may comprise a helically wound ribbon 12 as herein described, and a second portion 28 may comprise an alternative stent design, such as a prior art design. For example, the first portion 26 may comprise a first rail 20, a second rail 30 and a plurality of connector struts 40. The second portion 28 may comprise a plurality of serpentine bands 34, wherein adjacent serpentine bands 34 may be connected by connectors 35. The first portion 26 and the second portion 28 may be connected to one another using a connector 92 or any other suitable method. A connector 92 may connect at one end to the first portion 26 and at another end to the second portion 28. A connector 92 may connect to any part of the first portion 26, such as a rail 20, 30 or a connector strut 40. In some embodiments, multiple connectors 92 may connect a first portion 26 to a second portion 28.

Figure 16:
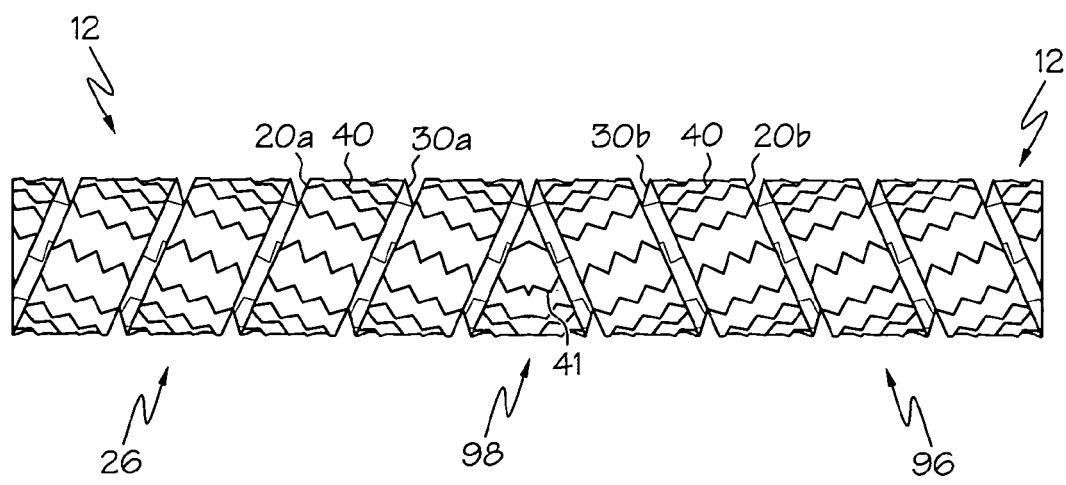
FIG. 16 shows another embodiment of an inventive stent.

FIG. 16 shows another embodiment of a stent 10, wherein a first portion 26 and a second portion 96 may each comprise a helically wound ribbon 12 as herein described. The ribbon 12 of the first portion 26 may wind in one direction, and the ribbon of the second portion 96 may wind in another direction. The first portion 26 may connect to the second portion 96 at a joining area 98, wherein the first rail 20a of the first portion may 26 connect to the first rail 20b of the second portion 96, and the second rail 30a of the first portion 26 may connect to the second rail 30b of the second portion 96. The joining area 98 may also include one or more common connector struts 41, which may extend from a rail 20, 30 of the first portion 26 to a rail 20, 30 of the second portion 96.

In some embodiments, a first portion 26 and a second portion 96 may be connected to one another via one or more connectors 92 (see FIG. 15). A connector 92 may connect at one end to any part of a first portion 26, and may connect at the other end to any part of a second portion 96.

In other embodiments, a stent 10 may comprise any number of individual portions, such as described with respect to FIGS. 15 and 16 (i.e. portions 26, 28, 96, etc.), connected in series. Adjacent portions may be connected by one or more connectors 92, by a joining area 98, or by any other suitable method. A stent 10 may comprise a long stent having a plurality of portions. The portions may be arranged in any desirable configuration. The portions may have any suitable shape and orientation with respect to one another. Various embodiments may be self-expanding or balloon expandable.

In some embodiments, a helically wound ribbon 12 stent may be used as a portion of a multilayer stent. The helically would ribbon 12 stent may be used in parallel with any other type of stent configuration. For example, the helically wound ribbon stent may comprise an inner stent, and a prior art design stent may comprise an outer stent. In another embodiment, a prior art design stent may comprise an inner stent, and a helically wound ribbon stent may comprise an outer stent. In some embodiments, a helically would ribbon 12 stent may comprise an inner stent and another helically would ribbon 12 stent may comprise an outer stent. The inner ribbon 12 stent may wind in one direction, and the outer ribbon 12 stent may wind in another direction.

The inventive stents 10 may have a substantially uniform diameter in the expanded and/or unexpanded states or may have a non-uniform diameter in the expanded and/or unexpanded state. Thus, for example, a portion of the stent 10 may have a continuous or a discontinuous taper in diameter. One or both of the ends of stent may have a wider diameter than the remainder of the stent or a narrow diameter. The stent may also have a generally increasing diameter from one end to the other.

In some embodiments, a stent 10 or ribbon 12 may include a closed cell 14 design. In some embodiments, a stent 10 or ribbon 12 may include at least on open cell or a plurality of open cells.

In some embodiments, a stent 10 may be self-expanding, formed from a shape memory material, spring steel or other materials which are capable of self-expanding. Examples of shape memory materials are provided below. Desirably, the stent 10 may self-expand to an expanded configuration. The stent 10 may be reduced to an unexpanded state and covered with a sheath or other constraining device. Desirably, in an unexpanded state, a ribbon 12 may be constrained to have an unexpanded width that is less than the width of the ribbon 12 in an expanded state. Upon removal of the sheath or constraining device, the stent 10 may self-expand to an expanded configuration.

In some embodiments, a stent 10 may be balloon expandable. In some embodiments, a stent 10 may be a combination balloon expandable/self-expanding stent, such as a stent comprising a portion of plastically deformable material and a portion of shape memory material.

Suitable medical devices such as those disclosed in U.S. Pat. Nos. 6,123,712, 6,120,522 and 5,957,930 may be used to deliver the inventive stents to the desired bodily location. The choice of delivery device will depend on whether a self-expanding or balloon expandable stent is used. The inventive stents may be delivered in conjunction with one or more stent retaining sleeves or socks. Examples of stent retaining sleeves are disclosed in US 20030065376A1, U.S. Pat. Nos. 6,607,552, and 6,432,129, the entire disclosures of which are incorporated herein by reference.

Upon delivery to a deployment site, an inventive stent may be expanded, wherein the diameter of the stent may increase and the width of the ribbon may increase.

The inventive stents may be manufactured using known stent manufacturing techniques. A stent may be formed by first forming a ribbon 12 and then helically winding the ribbon 12 to form a stent. A stent may also be formed directly in a tubular shape such as by performing manufacturing operations on a tube of material. For example, a framework having first and second rails and connector struts may be cut directly from a tube.

Suitable methods for manufacturing the inventive stents include laser cutting, laser ablating, chemical etching or stamping of a tube. The inventive stents may also be manufactured by laser cutting, laser ablating, chemically etching, or stamping a flat sheet, rolling the sheet and, optionally, welding the sheet. Other suitable manufacturing techniques include electrode discharge machining or molding the stent with the desired design. The stent may also be manufactured by welding individual sections together, for example by welding connector struts 40 to the first rail 20 and to the second rail 30. Any other suitable stent manufacturing process may also be used.

Any suitable stent material may be used in the manufacture of the inventive stents. Examples of such materials include polymeric materials, metals, ceramics and composites. Suitable polymeric materials include thermotropic liquid crystal polymers (LCP's), shape memory polymers, bioabsorbable polymers and the like. Where the stent is made of metal, the metal may be stainless steel, bioabsorbable alloys, cobalt chrome alloys such as elgiloy, tantalum or other plastically deformable metals. Other suitable metals include shape-memory metals such as nickel-titanium alloys generically known as "nitinol", platinum/tungsten alloys and titanium alloys and spring steel.

The invention also contemplates the use of more than one material in the inventive stents. For example, the connector struts 40 may be made from a different material than the first rail 20 or second rail 30. Some connector struts 40 may be made from different materials than other connector struts. Further, any individual member, such as a rail or connector strut, may be made from more than one material, and may include a first portion made from a first material and a second portion made from a second material.

The inventive stents may be provided in mechanically expandable form, in self-expanding form or as a hybrid of the two. Mechanically expandable stents, in accordance with the invention, may be expanded using any suitable mechanical device including a balloon and/or a catheter having one portion rotatable with respect to another portion. For example, a helically wound stent may be expanded using a catheter having a first portion connected to the first end of the stent and a second portion connected to the second end of the stent. The two portions may be rotated with respect to one another to cause an unwinding of the helical stent and a resulting increase in the stent diameter.

The inventive stents may include suitable coatings or markers to enhance visibility under fluoroscopy, MRI or the like. For example, the stents may be coated with gold or other noble metals or sputtered with tantalum or other metals. The stents may also be made directly from a radiopaque material to obviate the need for a radiopaque coating or may be made of a material having a radiopaque inner core. Other radiopaque metals which may be used include platinum, platinum-tungsten, palladium, platinum-iridium, rhodium, tantalum, or alloys or composites of these metals. In the case of MRI compatible stents, the stent will desirably be made of an MRI compatible material, as known in the art and optionally may be provided with MRI markers as known in the art.

In some embodiments the stent 10 may comprise one or more therapeutic agents. In some embodiments the agent is placed on the stent in the form of a coating. In at least one embodiment the coating includes at least one therapeutic agent and at least one polymer agent.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

In some embodiments, a stent may be provided with dimpled surfaces, holes, valleys and/or other indentations in order to hold a coating, such as a drug coating.

The inventive stents may also be provided with a sugar or more generally a carbohydrate and/or a gelatin to maintain the stent on a balloon during delivery of the stent to a desired bodily location. Other suitable compounds for treating the stent include biodegradable polymers and polymers which are dissolvable in bodily fluids. Portions of the interior and/or exterior of the stent may be coated or impregnated with the compound. Mechanical retention devices may also be used to maintain the stent on a balloon or catheter during delivery. To that end, the use of other coatings on the inventive stents is also within the scope of the invention.

The inventive stents may also be used as the framework for a graft. Suitable coverings include nylon, collagen, PTFE and expanded PTFE, polyethylene terephthalate and KEVLAR, or any of the materials disclosed in U.S. Pat. Nos. 5,824,046 and 5,755,770. More generally, any known graft material may be used including synthetic polymers such as polyethylene, polypropylene, polyurethane, polyglycolic acid, polyesters, polyamides, their mixtures, blends and copolymers.

The above disclosure is intended to be illustrative and not exhaustive. This description will suggest many variations and alternatives to one of ordinary skill in this field of art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A stent comprising a helically wound ribbon of material, the stent having a longitudinal axis extending therethrough, the ribbon having a width dimension, wherein the stent is constructed and arranged such that the width dimension of the ribbon in an expanded state of the stent exceeds the width dimension of the ribbon in an unexpanded state of the stent, the ribbon comprises a first rail and a second rail, the first rail connected to the second rail by a plurality of connector struts;
   wherein the first rail is slidably engaged with the second rail.

2. An unexpanded coil stent comprising:
   a strip helically wound about a longitudinal axis of the stent, the strip having a width dimension;
   the strip having a predetermined number of turns about the longitudinal axis, wherein upon expansion of the stent, the number of turns of the strip about the longitudinal axis decreases and the width dimension of the strip increases.

3. The stent of claim 2 wherein the strip comprises a plurality of loops which lengthen in the longitudinal direction of the stent upon expansion of the stent.

4. The stent of claim 2 wherein adjacent turns of the strip are separated by a gap, the gap spiraling continuously from one end of the stent to the other end of the stent.

5. The stent of claim 2 wherein adjacent turns of the strip are separated by a gap, the gap spiraling continuously at least 360° about the longitudinal axis of the stent.

6. The stent of claim 5 wherein in an unexpanded state, the width dimension of the strip is constant.

7. The stent of claim 2 wherein adjacent turns of the strip are separated by a gap, the gap spiraling continuously at least 720° about the longitudinal axis of the stent.

8. The stent of claim 2 wherein in an unexpanded state, the width dimension of the strip is constant.

9. The stent of claim 2 wherein in an unexpanded state, the width dimension of the strip varies over at least a portion of the strip.

* * * * *